United States Patent [19]

Morrey et al.

[11] Patent Number: 4,608,055
[45] Date of Patent: Aug. 26, 1986

[54] FEMORAL COMPONENT FOR HIP PROSTHESIS

[75] Inventors: Bernard F. Morrey; Edmund Y. S. Chao, both of Rochester, Minn.

[73] Assignee: Mayo Foundation, Rochester, Minn.

[21] Appl. No.: 570,094

[22] Filed: Jan. 12, 1984

[51] Int. Cl.⁴ .............................................. A61F 1/04
[52] U.S. Cl. ................................. 623/23; 128/92 C; 128/92 CA
[58] Field of Search .................... 3/1.9, 1.91, 1.911, 3/1.912, 1.913; 128/92 C, 92 CA, 92 E

[56] References Cited

U.S. PATENT DOCUMENTS

| | | | |
|---|---|---|---|
| 3,740,769 | 6/1973 | Habowsh | 3/1.912 |
| 3,906,550 | 9/1975 | Rostoker et al. | 3/1.912 |
| 4,051,559 | 10/1977 | Pifferi | 128/92 C |
| 4,167,047 | 9/1979 | Grundeir et al. | 128/92 C |
| 4,520,511 | 6/1985 | Gianezio et al. | 128/92 CA |

FOREIGN PATENT DOCUMENTS

| | | | |
|---|---|---|---|
| 0000549 | 2/1979 | European Pat. Off. | 3/1.91 |
| 2306552 | 8/1974 | Fed. Rep. of Germany | 3/1.91 |
| 1446097 | 8/1976 | United Kingdom | 3/1.91 |

Primary Examiner—Richard J. Apley
Assistant Examiner—David J. Isabella
Attorney, Agent, or Firm—Sherman & Shalloway

[57] ABSTRACT

An improved femoral component for use in a total hip replacement prosthesis comprises a stem portion and a combined head and neck portion. The stem portion includes a proximal portion and a distal portion which are angularly related with respect to one another and with the proximal portion including a recess formed therein for receipt of the tapered portion of the head and neck component. The head and neck component includes a substantially part spherical head portion attached to a neck portion and a tapered portion angularly attached to the neck portion via a basalar neck portion with the tapered portion being adapted to be permanently inserted into the recess portion of the proximal end of the above described stem portion. The stem portion includes a plurality of recesses on the periphery and longitudinal extent thereof which recesses receive fiber metal pads which are provided to allow bony ingrowth therein to retain the femoral component permanently installed in the proximal end of the femur.

1 Claim, 9 Drawing Figures

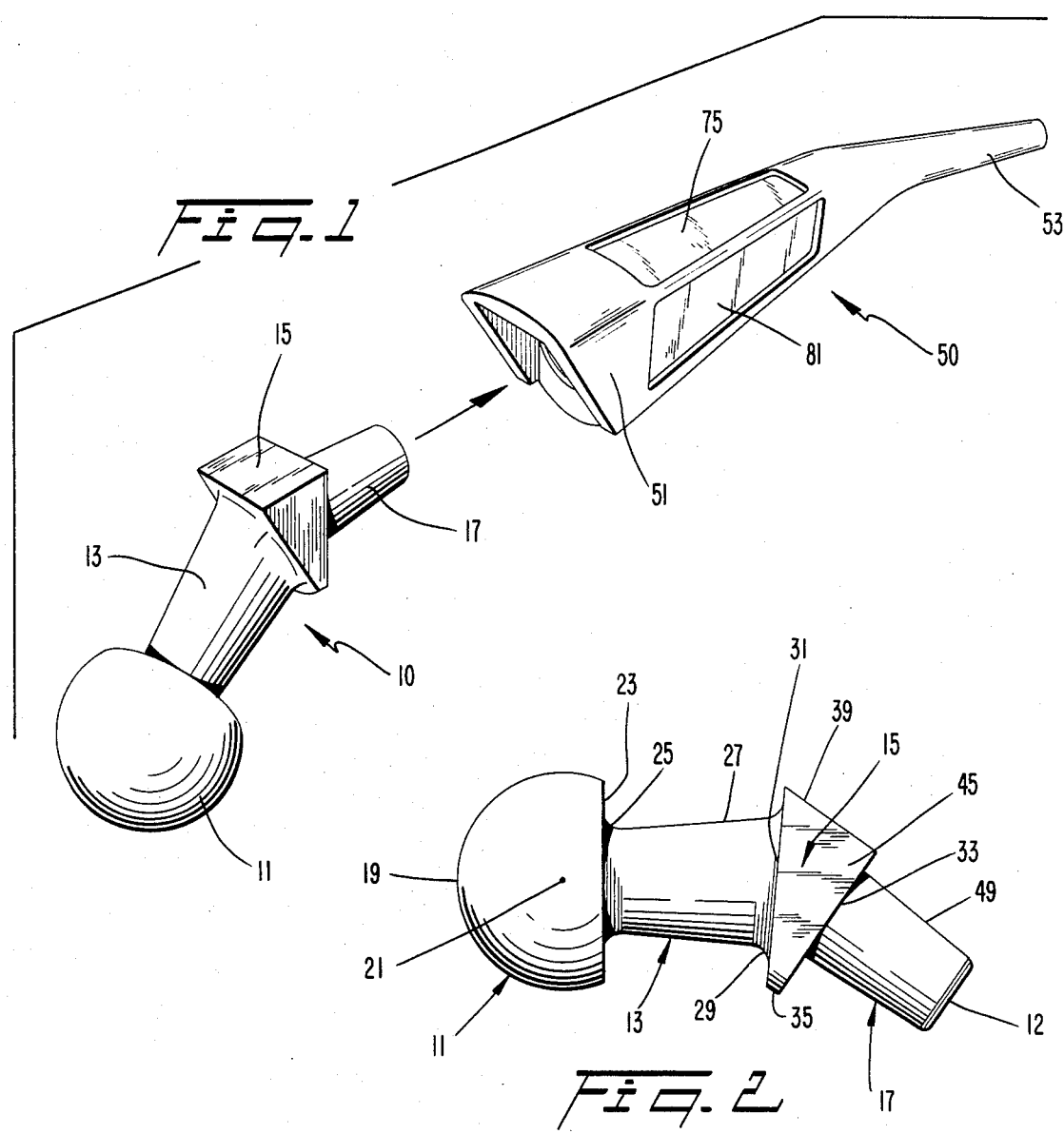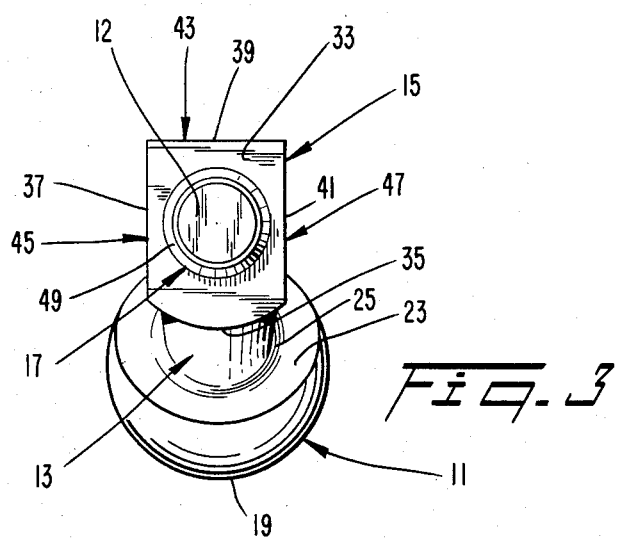

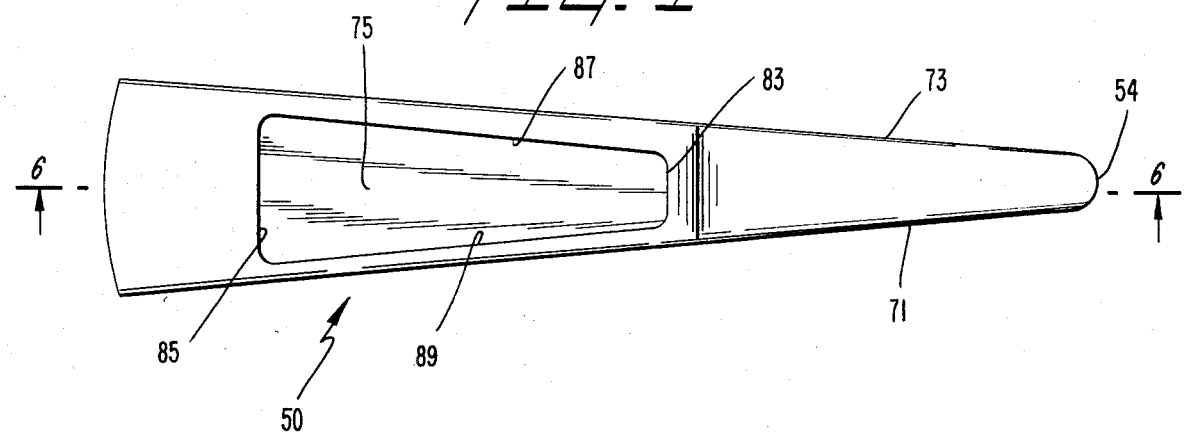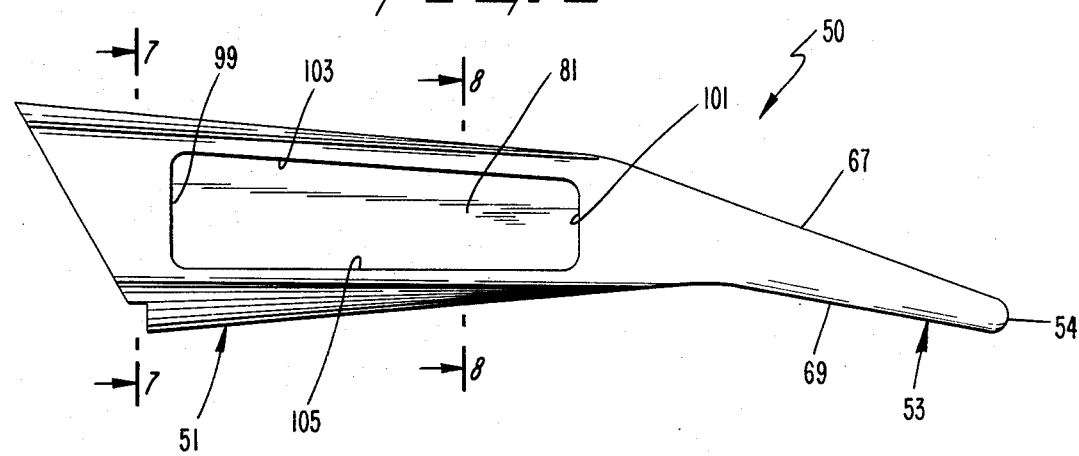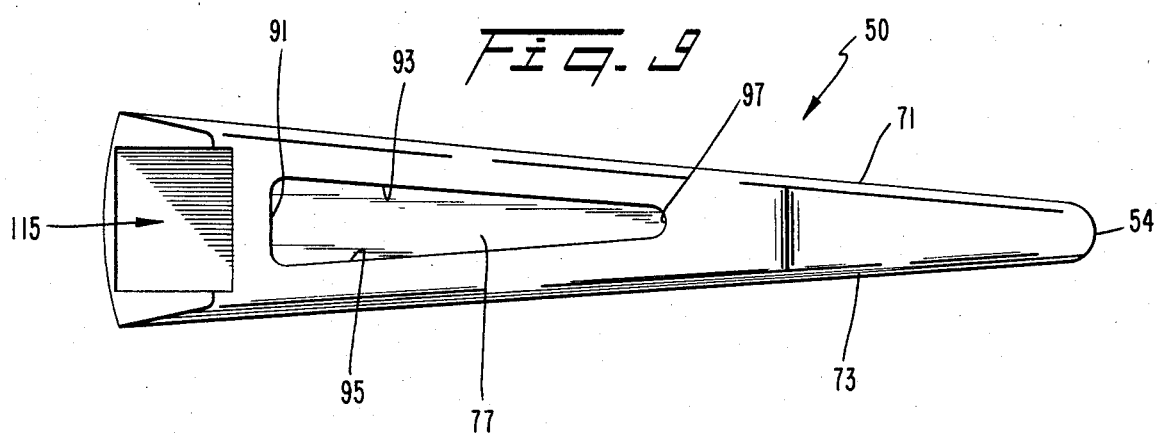

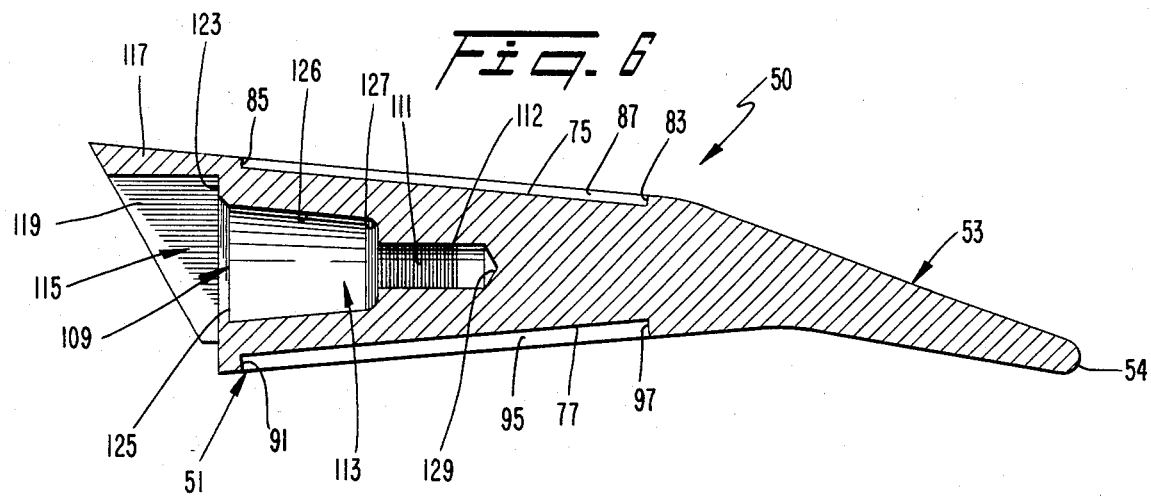
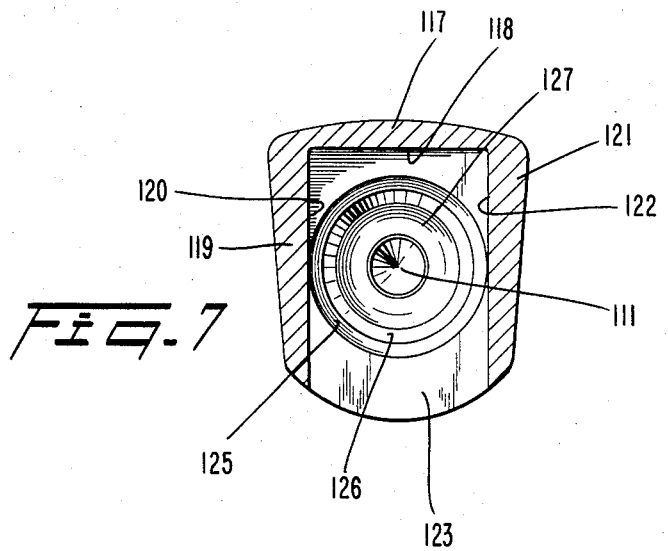
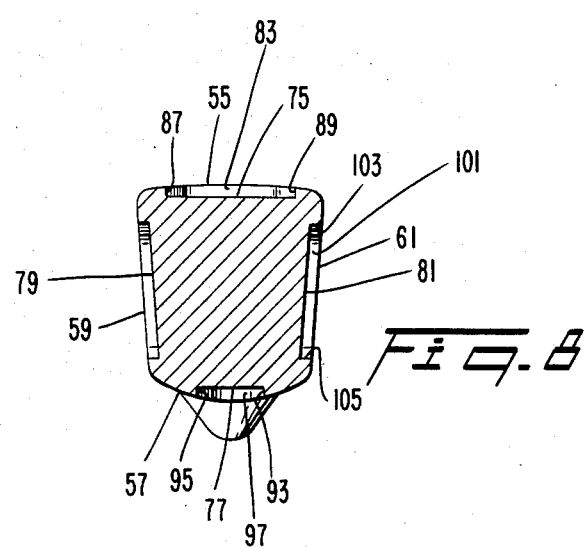

FEMORAL COMPONENT FOR HIP PROSTHESIS

BACKGROUND OF THE INVENTION

This invention relates to an improved femoral component which forms a part of a total hip replacement prosthesis system. The improved femoral component includes a stem portion and a head and neck portion with the head and neck portion having an end comprising a basalar neck portion and a tapered portion inserted into a recess formed at one end of the stem portion. The following prior art is known to applicant:

U.S. Pat. No. 3,067,740 to Habosh discloses a two part insert wherein the head and neck portion thereof is provided with a sleeve which fits over a threaded and splinted end of the stem and is secured with the cap nut. The stem is of a four lobed cross-sectional design and tapers from its proximal to its distal end.

U.S. Pat. No. 3,806,957 to Shersher discloses a femoral insert having a head and neck portion which has a threaded split shank which fits into a socket in the proximal portion of the shaft and is secured by a wedge-shaped screw lock.

U.S. Pat. No. 3,874,003 to Moser, et al. discloses an artificial hip prosthesis wherein the spherical head portion thereof has a recess which fits over a pin extending from a shoulder of the respective stem. At the region of the recess, the stem shoulder has a radially extending collar. Pegs located on the head cooperate with respective depressions in the collar to prevent relative rotation between the head and the pin.

U.S. Pat. No. 3,906,550 to Rostoker, et al. discloses a prosthetic device including a fiber metal attachment structure 18 which comprises a plurality of tubular fiber metal segments which surround the stem portion of the femoral component and promote bony ingrowth therein.

U.S. Pat. No. 3,918,441 to Getscher discloses a two piece insert designed to brace a fractured femur and includes a shaft and head portion which cooperate with one another to receive and distribute weight evenly through the bone. The shaft and head portion are joined by means of a tongue and groove connection and are retained in a joined configuration by a set screw.

U.S. Pat. No. 3,987,499 to Scharbach, et al. discloses a three part implant made of a metallic material coated with enamel and further comprising a threaded anchoring part to which is secured an angled transition part by means of a screw or bolt. The free end of the transition part is threaded to receive a ball head including an intermediary collar thereon.

U.S. Pat. No. 4,001,897 to Rambert, et al discloses a femoral prosthesis including a spherical head which includes a pin therewith which fits into a collar located on an associated shank and which is secured thereto by means of a bolt.

U.S. Pat. No. 4,030,143 to Elloy, et al. discloses a prosthesis intended for use in the shoulder area which includes a scapular component having a multitapered shank consisting of a wide portion at the area of the shoulder and which curves to a tapering tail portion at a remote location thereof.

U.S. Pat. No. 4,031,571 to Heimke, et al. discloses a hip endoprosthesis wherein the stem portion which is inserted into the femur is provided with a stepped configuration which acts to distribute the forces in the bone tissue. Aslo disclosed therein, is the use of a ceramic material which promotes bone formation on the surface of the implant.

U.S. Pat. No. 4,051,559 to Pifferi discloses a two piece femoral insert wherein the head and neck portion thereof is angularly attached to a wedged portion from which depends a pin member. The pin member fits into the upper portion of a cylindrical helically threaded hollow shank and is secured therein in a fixed manner by means of a threaded bolt.

U.S. Pat. No. 4,068,324 to Townley, et al. discloses a hip joint prosthesis including a femoral portion made of one piece. The femoral portion includes a head and neck which neck merges into a platform from which depends an elongated stem portion which is inserted into the medullar cavity of the femur.

U.S. Pat. No. 4,115,875 to Rambert, et al. discloses a femoral prosthesis having a shank the upper face thereof being provided with a bore which is threaded toward the bottom thereof. The femoral head has a conically shaped neck with corresponding threads to engage those in the above described bore.

U.S. Pat. No. 4,261,063 to Blanquaert discloses a femoral insert having a stem of irregular shape which is surrounded by a lattice of titanium wire of a mesh size. The stem has longitudinal grooves and transverse notches and may, if desired, also be made of a titanium alloy containing, for example, six percent aluminum and four percent vanadium. The lattice structure above described is attached to the stem by means of two strips of titanium or other alloy which are placed on the outside of the lattice and electron welded to the stem.

European Pat. No. 001,743 to Schider discloses a joint prosthesis including a ball 1 attached to a neck 2 at 6. The neck 2 is inserted into a cavity formed in a stem portion 3 which stem portion 3 is inserted into the femur.

A publication entitled "The Original M. E. Muller Straight Stem-Femoral Head Prostheses" discloses a femoral component including a stem portion with a neck extending upwardly therefrom and a head portion having a hole therein which fits over the stem neck. As disclosed therein, the device includes a plurality of different stem sizes and a plurality of different head sizes which may be combined together to form a femoral component of the proper size for a particular use.

Publication entitled "BETA Universal Hip System" discloses a femoral component including a head portion with a hollow neck which fits over an upstanding portion of the respective stem.

SUMMARY OF THE INVENTION

The improved femoral component disclosed herein overcomes the drawbacks and limitations of the prior art as described above by providing a femoral component including the following unique combination of features:

(a) The femoral component of the present invention is comprised of two parts, a head and neck portion and a stem portion.

(b) The stem portion comprises an elongated member including a proximal portion and a distal portion which are angularly related with respect to one another.

(c) The stem portion includes large area recesses on its faces in which are attached fibrous metal pads which are adapted to allow bony ingrowth therein to aid in retention of the prosthesis in its inserted position.

(d) The stem portion is wedge shaped in both the sagittal and coronal planes and this configuration is intended to permit the prosthesis to seat tightly into the bone bed so that stable motionless fixation is achieved at the time of surgery or subsequently with load. Such motionless fixation enables the bone tissue to grow into the pores formed as an integral part of the above noted fibrous metal thus ensuring permanent fixation.

(e) Due to the novel features of the invention, the prosthesis does not include a calcar collar either on the stem portion or on the head and neck portion.

(f) The distal end of the stem portion is tapered in an elongated fashion and terminates at a radiused end portion. In the coronal plane, the tapered portion is angulated in a valgus direction from the axis of the main body of the stem portion. This enables the stem portion to be oriented and positioned in the bone tissue during the insertion thereof.

(g) In the proximal portion of the stem portion, a shoulder is provided into which a recess is cut, which recess accepts the basalar neck portion of the prosthesis.

(h) At the bottom of the above described shoulder recess, and approximately centered on a center line of the body of the stem portion, a substantially cylindrical socket-like cavity with a slight taper therein is cut into the interior walls of the stem portion which cavity is provided to receive a similarly tapered portion of the head and neck portion of the prosthesis. This male tapered portion is designed and intended to mate tightly with the socket-like cavity of a stem portion.

(i) The head and neck portion includes a centrally located wedge shaped basalar neck portion which has the above described male tapered portion protruding from one face thereof and further has the head portion thereof attached to another angularly opposed face thereof through a neck portion. The wedge shaped basalar neck portion is designed so as to fit into the shoulder recess described above.

(j) In view of the fact that the femoral component is made of two separate portions which are attached together, a system of respective stem portions and head and neck portions may be provided as an aspect of this invention so that different head and neck portions and dimensions may be coupled with different stem portions so as to achieve an improved femoral component which includes components adaptable to a large variety of sizes and configurations of human hip regions.

Accordingly, it is a first object of the present invention to provide a femoral component for a total hip replacement prosthesis which is made of two parts, a stem portion and a head and neck portion.

It is a further object of the present invention to provide the femoral component stem portion with an angular design and with recesses in the peripheral faces thereof.

It is a yet further object of the present invention to provide such recesses with fibrous metal inserts therein which promote bony ingrowth of adjacent bone tissue to aid in retaining the implant in it installed position.

It is a yet further object of the present invention to make the head and neck portion thereof of an angular shape including a substantially spherical head portion attached to a wedge shaped basalar neck portion through a neck portion.

It is a yet further object of the present invention to provide an angularly opposed face of the wedge shaped basalar neck portion with a tapered portion which is insertable into a recess formed in the proximal end of the stem portion.

It is a further object of the present invention to provide the femoral component in two separable parts so as to enable attaching of different sized head and neck portions with different sized stem portions to thereby enable use of the present invention with hips of differing configurations.

These and other objects, advantages and features of the invention will become more apparent to those skilled in the art after reading the following description of the preferred embodiment of the invention in connection with the appended drawing figures.

BRIEF DESCRIPTION OF THE DRAWINGS

FIG. 1 shows an exploded perspective view of the invention.

FIG. 2 shows a side view of the head and stem portion of the present invention.

FIG. 3 shows a view from above the wedge shaped basalar neck portion and tapered portion of the head and neck portion of the invention.

FIG. 4 shows a top view of the stem portion of the present invention.

FIG. 5 shows a side view of the stem portion of the present invention.

FIG. 6 shows a cross-sectional view along the line 6—6 of FIG. 4.

FIG. 7 shows a cross-sectional view along the lines 7—7 of FIG. 5.

FIG. 8 shows a cross-sectional view along the line 8—8 of FIG. 5.

FIG. 9 shows a bottom view of the stem portion of the present invention.

SPECIFIC DESCRIPTION OF THE PREFERRED EMBODIMENT

FIG. 1 shows an exploded perspective view of the device with the head and neck portion 10 shown adjacent to the stem portion 50 and oriented with respect to the stem portion such that linear motion of the head and neck portion 10 toward the stem portion will result in installation of the head and neck portion 10 on the stem portion 50. FIGS. 4–9 show the stem portion to include a proximal portion 51 and a distal portion 53. As best seen in FIGS. 5 and 6, the proximal portion 51 and the distal portion 53 are angularly related with respect to one another. In particular, and as best shown in FIG. 8, the device has a substantially square cross-section including a top surface 55, a bottom suface 57 and side surfaces 59 and 61. As shown in FIG. 8, the top and bottom surfaces 55 and 57 are slightly concave and the side surfaces 59 and 61 taper toward one another in the direction from the top surface 55 to the bottom surface 57. Referring back to FIGS. 5 and 6, the bottom surface 57 includes a location 63 and the top surface 55 includes a location 65 which locations 63 and 65 define the transition point from the proximal end 51 to the distal end 53 of the stem portion 50. The distal portion 53 includes respective top and bottom surfaces 67 and 69 which form obtuse angles with the respective surfaces 55 and 57. As shown in FIGS. 4 and 9, the distal portion 53 also includes side surfaces 71 and 73 which are substantially parallel to the side surfaces 59 and 61 of the proximal portion 51. As can be seen from FIGS. 4 and 8, the side walls 59 and 61 have a dual taper, tapering both from the direction of the top wall 55 to the bottom wall 57 and from the proximal end to the distal end of the proximal portion 51.

As shown in FIGS. 4–6 and 8–9, each of the surfaces 55, 57, 59 and 61 includes a recess therein with the top surface 55 having a recess 75, the bottom surface 57 having a recess 77 therein, the side surface 59 having a recess 79 and the side surface 61 having a recess 81. As shown in FIG. 4, the recess 75 is trapezoidal in shape including top and bottom edges 83 and 85 and tapered side edges 87 and 89. Referring to FIG. 9, the bottom recess 77 is approximately triangular in shape including a base edge 91 and side edges 93 and 95 which converge to a radiused converging end 97. FIG. 5 shows the recess 81 which is substantially identical to the recess 79. The recess 81 is also trapezoidal and includes top and bottom edges 101 and 99 and side edges 103 and 105. It is noted that side edge 105 is substantially perpendicular to both top edge 101 and bottom edge 99 while side edge 103 is tapered with respect to top edge 101 and bottom edge 99. The recesses 75, 77, 79 and 81 are provided in the proximal portion 51 of the stem portion 50 for receipt of fibrous metal pads 107 which in the preferred embodiment are sintered into the respective recesses so as to fixedly retain the pads 107 therein. The pads 107 in the preferred embodiment are made of an alloy of titanium, aluminum and vanadium trademarked by Zimmer Incorporated under the trademark "Tivanium" and are included in the device to facilitate ingrowth of bony tissue from adjacent bone surfaces into the pads 107 to thereby provide a means for permanently retaining the stem portion 50 in its installed position. It is noted here that the distal end 53 of the stem portion 50 has at its extreme end a radiused tip 54 which as best seen by comparing FIGS. 4 and 5 is radiused about a relatively large radius in a horizontal plane therethrough (FIG. 4) and is radiused about a relatively smaller radius in a vertical plane (FIG. 5).

With further reference, in particular, to FIGS. 6, 7 and 9, the proximal portion 51 of the stem portion 50 is seen to further include a stepped cavity 109 which is comprised of a first cavity portion 111, a second somewhat larger cavity 113, and a third outer most cavity 115. The cavity 115 is defined by a top wall 117 and two side walls 119 and 121 which as best shown in FIG. 6 are triangular in configuration. The innermost portion of the outermost cavity 115 is defined by a shoulder 123 which at its radially innermost extent merges into a chamfer 125 which defines the open mouth of the second cavity portion 113. As best seen in FIG. 6, the second cavity portion 113 has walls 126 which taper from a larger diameter area at mouth 125 to a smaller diameter at the area of radiused shoulder 27 which forms the mouth for the first cavity portion 111. The first cavity portion 111 is a substantially cylindrical entity whose innermost portion comprises a chamfered surface 129. The first cavity portion 111 is provided with screw threads 112 on its outer periphery for a purpose to be described hereinafter. The cavity 109 formed by cavity portions 111, 113 and 115 is provided to receive permanently assembled thereto the tapered portion and basalar neck portion of the head and neck 10 portion of the femoral component 1 as will be described hereinafter.

Referring now, in particular, to FIGS. 1, 2 and 3, the head and neck portion 10 of the femoral component 1 is seen to include a head portion 11, a neck portion 13, a basalar neck portion 15 connected to the end of the neck portion 13 remote from the head portion 11 and a tapered portion 17 connected to a face of the basalar neck portion substantially remote from the face to which the neck portion 13 is connected. The structure of the head and neck portion 10 may be best seen with reference to FIG. 2. As shown in FIG. 2, the head portion 11 includes a spherical outer surface 19 which has a slightly greater extent than a hemisphere. In this regard, the surface 19 is centered at point 21 and it can be seen from FIG. 2 that the surface 19 distal of the point 21 is concavely convergent to an annular shoulder portion 23. The neck portion 13 is connected to the annular shoulder portion 23 through an annular radiused portion 25. The neck portion 13 includes an outer substantially conical wall 27 which diverges from the annular radiused portion 25 to its largest dimension where it merges with an annular radiused portion 29. As shown in FIG. 2, the annular radiused portion 29 is substantially located in a plane which makes an acute angle with a plane extending through the annular radiused portion 25. The annular radiused portion 29 connects the neck portion 13 with the basalar neck portion 15. The basalar neck portion 15 includes a proximal face 31 at the annular radiused portion 29 and further includes a distal face 33. The proximal and distal faces 31 and 33 converge at a curved surface 35, best shown in FIG. 3, with the faces 31 and 33 making an acute angle therebetween, as best seen in FIG. 2. Referring again to FIG. 3, the distal face 33 is seen to comprise edges 37, 39 and 41 as well as the edge corresponding to the curved surface 35. The edges 37, 39 and 41 are substantially straight while as explained above the surface 35 is curved. The basalar neck portion 15 is comprised of a flat top surface 43 and two substantially triangularly shaped side surfaces 45 and 47 with the face 45 being shown in FIG. 2. The tapered portion 17 protrudes outwardly from the face 33 of the basalar neck portion 15 and is of generally trucated conical configuration. The tapered portion includes a substantially conical outer wall portion 49 and a substantially flat end 12.

It is noted that the angle of taper of the surface 126 of the cavity portion 113 is intended to be the same as the angle of taper of the surface 49 of the taper 17. Furthermore as noted in FIG. 7, the wall 117 includes an inner surface 118, the wall 119 has an inner surface 120 and the wall 121 has an inner surface 122.

The head and neck portion 10 and the stem portion 50 having now been described, the method of using the femoral component 1 will be now explained. Prepartory to the insertion of the stem portion 50 into the femur, a cavity is formed within the femoral tissue sized so as to receive in an interference fashion the stem 50. After this cavity is formed, the stem portion 50 is inserted therein to provide the above described interference fit therein. When installed, the fibrous metal inserts 107 will engage adjacent bone tissue in all planes of the proximal end 51 of the stem portion 50. At this juncture, it is noted that the fibrous metal inserts 107 may be made of any wire mesh material facilitating bony ingrowth into the pores therein. Further, if desired, the inserts 107 may be made of a titanium bead material or, if desired, of any material including titanium which allows biological fixation therewith.

After the stem portion 50 has been inserted into the femur in the proper orientation, the head and neck portion 10 is installed onto the stem portion 50. With particular reference to FIGS. 1, 2, 3 and 6, the head and stem portion 10 is inserted into the stem 50 as follows: the tapered portion 17 is inserted into the substantially conical cavity 113 of the stem portion 50 with the tapered outer surface 49 of the tapered portion 17 engaging the tapered inner surface 126 of the cavity portion 113. It is noted that the angle of taper of the surfaces 49 and 126 is preferably substantially identical and in the preferred embodiment of the present invention is made from 4-6 degrees with respect to a line comprising the longitudinal axis of the respective tapered portion 17 and the cavity portion 113. With the tapered portion 17 located within the cavity portion 113, the rectangular basalar neck portion 15 is so oriented such that the surfaces 120, 118 and 122 of the proximal portion 51 of the stem portion 50 are in engagement with respective surfaces 47, 43 and 45 on the rectangular basalar neck portion 15. With this orientation, the curved surface 35 is thereby aligned with the bottom surface 57 of the proximal portion 51 of the stem portion 50. This interaction between the surfaces 120, 118 and 122 and the respective surfaces 47, 43 and 45 ensures alignment of the head and neck portion 10 in the proper orientation with respect to the stem portion 50. With the head and neck portion 10 so aligned with respect to the stem portion 50, the head and neck portion 10 is linearly pushed into the cavity portions 113 and 115 until an interference fit develops between the surfaces 49 and 126 and the surface 33 of the rectangular basalar neck portion 15 rests against the shoulder portion 123 of the cavity portion 115. Due to the interference nature of the fit between the surfaces 49 and 126, no mechanical or chemical fixation is necessary to hold the head and neck portion 10 in permanent securement to the stem portion 50. As such, no screws, cement or other means of securement are used and the large surface area of engagement between the surface 49 on the taper 17 and the surface 126 in the cavity portion 113 is sufficient to maintain the two components 10 and 50 securely attached to one another.

Making the femoral component one of two attachable parts enables the achievement by the surgeon of great flexibility in the installation thereof. With this separate component approach, the surgeon may choose from a variety of head and neck portions 10 of differing sizes and configurations as well as from a variety of stem portions 50 of different sizes and configurations so that the particular characteristics of a particular hip may be taken into account in choosing the prosthesis which is most suitable for the particular purpose. For example, the head and neck portion 10 may come in a variety of sizes with, for example, the head portion 11 being made with diameter of from 40 millimeters to 60 millimeters with as many as 8 to 10 different sizes of head available therebetween.

As noted above, the cavity portion 111 of the stem portion 50 includes threads 112 on its interior surface. These threads 112 are provided so that if it becomes necessary for some reason to remove the femoral component 1 from the bone tissue, this may be done first by applying great force to remove the head and neck portion 10 from the stem portion 50 and thereafter threading a long bolt into the cavity portion 111 which bolt will have exterior threads complimentary to the threads 112 thereof and which bolt (not shown) will provide a means which may be gripped by a tool or machine to facilitate the pulling of the stem portion 50 out of the bone tissue.

It is noted with respect to the present invention that the femoral component 1 may be used in conjunction with any acetabular component which a surgeon determines will be compatible therewith, for example, the spherical bearing surface 6 of the above discussed U.S. Pat. No. 4,001,897 Rambert, et al. would appear to be suitable for use in conjunction with the femoral component 1 of the present invention.

Although a preferred embodiment of the femoral component 1 has been described with some particularity, many modifications and variations in the invention may occur to one skilled in the art in light of the above teachings. It is therefore to be understood that it is intended that the invention described herein should only be limited by the scope of the following claims.

We claim:

1. In an improved femoral component including a stem component and a head and neck component connectable to said stem component to form said femoral component, said head and neck component comprising:
   (a) a head portion;
   (b) a neck member at a first end thereof protruding from a substantially flat face of said head portion;
   (c) said neck member, at a second end thereof being connected to a first surface of a basalar neck portion;
   (d) said basalar neck portion having a second surface from which protrudes a tapered portion, a third substantially rectangular surface substantially perpendicular to said second surface, and fourth and fifth surfaces substantially perpendicular to both said second surface and said third surface; and
   (e) said neck member and said tapered portion forming an obtuse angle with one another and said first and second surfaces converging to form an acute angle therebetween.

* * * * *